United States Patent
Wolf et al.

(10) Patent No.: US 7,183,266 B2
(45) Date of Patent: *Feb. 27, 2007

(54) DUAL INDUCED VISCOSITY FIBER SYSTEM AND USES THEREOF

(75) Inventors: Bryan W. Wolf, Johnstown, OH (US); Bruce B. Blidner, Westerville, OH (US); Keith A. Garleb, Pickerington, OH (US); Chron-Si Lai, Blacklick, OH (US); Timothy W. Schenz, Powell, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/157,298

(22) Filed: May 29, 2002

(65) Prior Publication Data

US 2003/0125301 A1 Jul. 3, 2003

Related U.S. Application Data

(60) Provisional application No. 60/294,817, filed on May 31, 2001.

(51) Int. Cl.
*A61K 31/715* (2006.01)
*A61K 31/70* (2006.01)
*A61K 47/00* (2006.01)

(52) U.S. Cl. .............................. 514/54; 514/2; 514/23; 514/57; 514/60; 514/775; 514/777; 514/866; 514/449; 536/2; 536/114; 426/2; 426/618; 426/72; 426/549; 435/232

(58) Field of Classification Search .................... 514/2, 514/23, 54, 57, 60, 775, 777, 866, 909, 14, 514/328, 449; 536/2, 114; 426/2, 618, 72, 426/549, 74; 435/232; 549/328
See application file for complete search history.

(56) References Cited

U.S. PATENT DOCUMENTS 4,556,578 A * 12/1985 Meyer ........................ 426/649

(Continued)

FOREIGN PATENT DOCUMENTS

| EP | 0768043 A2 | 10/1996 |
| GB | 2 079 129 A | 1/1982 |
| JP | 03-290157 | 12/1991 |
| WO | WO 96/25054 | 8/1996 |

OTHER PUBLICATIONS

Glytrol, 1995 Clintec Nutrition Company.

(Continued)

*Primary Examiner*—Shaojia Anna Jiang
*Assistant Examiner*—Devesh Khare
(74) *Attorney, Agent, or Firm*—William J. Winter

(57) ABSTRACT

The present invention relates generally to a method of blunting the postprandial glycemic response to a meal by feeding a dual induced viscosity fiber system. The first component of the induced viscosity fiber system is soluble fiber. The second component of the induced viscosity fiber system is water-insoluble, acid-soluble multivalent cations. The third component of the induced viscosity fiber system in lightly hydrolyzed starch. The fiber system will typically be incorporated into a meal replacement nutritional. The present invention also refers to a method of delivering soluble fiber to diabetics and to persons needing to lose weight. Additionally, the invention refers to a method of promoting the feeling of fullness and satiety by feeding a nutritional product containing the induced viscosity fiber system.

8 Claims, 2 Drawing Sheets

U.S. PATENT DOCUMENTS

| | | | |
|---|---|---|---|
| 5,085,883 | A | 2/1992 | Garleb et al. |
| 5,232,733 | A * | 8/1993 | Resmer ............... 426/590 |
| 5,292,723 | A | 3/1994 | Audry et al. |
| 5,470,839 | A | 11/1995 | Laughlin et al. |
| 6,020,017 | A | 2/2000 | Mingione |
| 6,221,836 | B1 | 4/2001 | Beale et al. |
| 6,248,375 | B1 * | 6/2001 | Gilles et al. ............ 426/72 |
| 6,429,190 | B1 * | 8/2002 | Portman ................ 514/2 |
| 6,733,769 | B1 | 5/2004 | Ryan et al. |
| 6,774,111 | B1 * | 8/2004 | Wolf et al. ............ 514/23 |
| 6,916,796 | B2 * | 7/2005 | Wolf .................... 514/54 |

OTHER PUBLICATIONS

Compelling Comparisons Glucerna®, Mar. 1996, Ross Products Division, Abbott Laboratories.
PediaSure®, Mar. 2001, Pediatric Nutritionals Product Guide, Ross Products Division, Abbott Laboratories.
Choice*dm*™, 1997 Mead Johnson & Company.
Resource® Diabetic, 1995 Clinical Products Division, Sandoz Nutrition Corporation.
Compelling Comparisons Glucerna®, 1996 Ross Products Division, Abbott Laboratories.
Brutomesso, D,; Briani, G,; Bilardo, G,; Vitale, E,; Lavagnini, T,; Marescotti, C,; Duner, E,; Giorato, C,; Tiengo, A, The medium-term effect of natural or extractive dietary fibres on plasma amino acids and lipids in type I diabetics.*Diabetes Research and Clinical Practice*. 1989, 6, 149-155.
Krotkeiewski, M., Effect of Guar Gum on Body-Weight, Hunger Ratings and Metabolism in Obese Subjects. *Br. J. Nutr*, 1984, 52, 97-105.
Multivalent cations, The Merck Index, $10^{th}$ edition.
"Fermentability of Various Fiber Sources by Human Fecal Bacteria In Vitro", American Journal Clinical Nutrition, 1991; 53: 14181424.
Garner, D.M.; Garfinkel, P.E. The Eating Attitudes Test: an index of the symptoms of anorexia nervosa. *Psychol. Med.* 1979, 9, 273-280.
Stunkard, A.J.; Messick, S. The three-factor eating questionnaire to measure dietary restraint, disinhibition, and hunger. *J. Psychosom. Res*.1985, 29, 71-83.
Zung, W.W.K. A self-rating depression scale.*Arch. Gen. Psychiatry* 1970, 12, 63-70.
The Alginate Reduce the Post prandial Glycaemic Response by Forming a Gel with Dietary Calcium in the Stomach of the Rat, *International Journal for Vitamin and Nutrition Research* (1997) 67 (1), 55-61.
JAPIO abstract AN 1991-290157 for JP 03-290157, Dec. 1991.
GPC Naturally (Collateral)—Maltodextrins and Corn Solids for Food Formulations, 1996.

* cited by examiner

DUAL INDUCED VISCOSITY FIBER SYSTEM AND USES THEREOF

CROSS REFERENCE

This application is a continuation-in-part of U.S. Ser. No. 60/294,817, filed on May 31, 2001. This application is related to U.S. Ser. No. 10/157,297, filed May 29, 2002 (now U.S. Pat. No. 7,067,498), and U.S. Ser. No. 10/157,296, filed May 29, 2002, the contents of which are incorporated herein by reference.

TECHNICAL FIELD

The present invention relates generally to a method of blunting the postprandial glycemic response to a meal. The invention also relates to an induced viscosity fiber system and the liquid products that incorporate the induced viscosity fiber system. Further, the invention relates to a method of incorporating soluble fiber into a liquid product without the typical negative organoleptic or physical stability issues. The invention also relates to a method of inducing the feeling of fullness and satiety by feeding the induced viscosity fiber system.

BACKGROUND OF THE INVENTION

Diabetes is the seventh leading cause of death in the United States and the sixth leading cause of death by disease among Americans. It is estimated that 15.7 million people, or 7.8% of the US population, suffer from diabetes. Consequently, the economic burden of diabetes is great, with an estimated total annual economic cost of $98 billion in 1997. This includes $44 billion for direct medical and treatment costs, and $54 billion for indirect costs due to disability and mortality.

The cause of diabetes is unknown, however, known risk factors for this disease are multi-factorial. Genetics and environmental factors such as obesity and sedentary lifestyle appear to contribute to diabetes incidence. Type 2 diabetes, a disorder resulting from the body's inability to make enough or properly use insulin, accounts for 90 to 95 percent of all diabetes. This type of diabetes is reaching epidemic proportions in America because of the increasing age of the population, in addition to a greater prevalence of obesity and sedentary lifestyles.

Standard treatment of diabetes involves maintenance of as near-normal blood glucose levels as possible by balancing food intake with insulin or oral glucose-lowering medications and physical activity levels. Low calorie diets and weight loss usually improve short-term glycemic levels and have the potential to improve long-term metabolic control. However, traditional dietary strategies, and even very-low-calorie diets, have usually not been effective in achieving long-term weight loss.

Obesity is associated with numerous chronic diseases, such as type 2 diabetes, heart disease, hypertension, stroke, dyslipidemia, osteoarthritis, sleep apnea, gallbladder disorders, respiratory problems, and malignancy. A loss of only 5% to 10% of baseline weight in an obese patient with type 2 diabetes, hypertension, or dyslipidemia can improve glycemic control, decrease blood pressure, and improve the lipid profile, respectively. Lifestyle modification by changes in diet or increase in exercise is usually the first step in treating overweight or obese persons. However, behavioral modification is often not very successful, and long-term maintenance of diet or exercise changes is attained by less than 15% of persons who initiate these changes. In addition, restricted calorie diets cannot be continued over a long period of time, and the majority of the weight lost on these diets is re-gained.

One approach to initiating and maintaining weight loss in overweight individuals is by inducing satiation (feeling of fullness during a meal) and satiety (feeling of fullness after a meal). Various gastrointestinal mechanisms trigger both the initiation and termination of eating in individual persons. Although gastric distention is a normal sign of "fullness" and plays a role in controlling food intake, its effects are temporary and distinct from feelings of satiety associated with a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.

The concept that dietary fiber may aid in the treatment of hyperglycemia has been suggested since the 1970's. Viscous soluble fiber (e.g., guar gum, psyllium, oat β-glucan) supplementation to test meals has been shown to effectively blunt postprandial glycemia. Despite the existence of some in vivo evidence; however, there is still considerable doubt about the efficacy of dietary fiber in the treatment of hyperglycemia. This doubt may exist because different types of dietary fibers have different physiological effects. As analytical methods for dietary fiber improve, so does our understanding of physiological fiber effects. For example, soluble viscous fibers generally have a greater effect on carbohydrate metabolism in the small intestine by slowing the rate of absorption, although delayed gastric emptying also may play a role. These phenomena should decrease the rate at which glucose enters the systemic circulation and delay the postprandial rise in blood glucose. While the applicability of this concept is evident, its clinical use is limited. Unfortunately, foodstuffs containing viscous fibers (e.g., guar gum) usually exhibit slimy mouth-feel, tooth packing, and poor palatability. The overall hedonic quality of guar-containing foods can be improved by reducing the average molecular weight (e.g., through chemical hydrolysis) of the galactomannan in guar gum; however, this results in a concurrent loss in clinical efficacy.

There are commercially available nutritional products that are designed to meet the nutritional needs of a diabetic while helping to maintain control of their blood glucose level. The commercial products are typically liquid and include higher amounts of fat. The higher fat is desired in a liquid nutritional as the fat slows down stomach emptying, thereby delaying the delivery of nutrients to the small intestine, which blunts the absorption curve of carbohydrates after a meal. Examples of typical commercial products for the diabetic population include Glucerna® (Ross Products Division of Abbott Laboratories, Columbus Ohio), Choice dm® (Mead Johnson & Company, Evansville, Ind.), Resource® Diabetic (Sandoz Nutrition Corporation, Berne, Switzerland), and Ensure® Glucerna(® Shake (Ross Products Division of Abbott Laboratories; Columbus Ohio).

The commercial product listed above typically use multi-component carbohydrate systems to blunt the glycemic response. The carbohydrate systems require multiple sources of carbohydrate that are absorbed.at different rates. These multi-component carbohydrate systems possess physical characteristics that make incorporation of the carbohydrate systems into nutritional formulas difficult. Additionally, these multi-component carbohydrate systems are often found to possess unacceptable organoleptic characteristics. For example, guar gum functions to provide viscosity in the stomach, thereby slowing the release of nutrients to the small intestine. Unfortunately, foodstuffs containing guar gum typically exhibit slimy mouth-feel, tooth packing, and poor palatability. Additionally, effective amounts of guar gum increase the viscosity of liquid products such that the liquid product gels in the container. The overall hedonic quality of guar-containing foods can be improved by reducing the average molecular weight (i.e., through hydrolysis) of the galactomannan in guar gum; however, this results in a concurrent loss in clinical efficacy. In addition to the challenge of making a palatable product, dietary supplementation with clinically effective levels of guar gum is also associated with gastrointestinal side effects (e.g., flatulence and diarrhea) from its colonic fermentation, because guar gum is a rapidly fermented carbohydrate.

Thus, a need has developed in the art for a fiber system which acts to blunt the absorption curve of carbohydrates after a meal, while being well tolerated, organoleptically acceptable and easily incorporated into nutritional matrixes. The formulation of these novel products that attenuate the postprandial glycemic excursion would enhance the use of nutrition as adjunctive therapy for people with diabetes mellitus.

The disease state of many diabetics is complicated by their overweight status. As described above, highly viscous digesta results in the slow release of nutrients to the small intestine. This slow release also induces the feeling of fullness and satiety. For example, 9 to 20 gm/day of supplemental guar gum for 4 to 8 weeks has been shown to significantly reduce body weight and sensations of hunger compared to control. (Bruttomesso, D.; Briani, G.; Bilardo, G.; Vitale, E.; Lavagnini, T.; Marescotti, C.; Duner, E.; Giorato, C.; Tiengo, A. The medium-term effect of natural or extractive dietary fibres on plasma amino acids and lipids in type 1 diabetics. *Diabetes Research and Clinical Practice.* 1989, 6, 149–155; Krotkiewski, M. Effect of guar gum on body-weight, hunger ratings and metabolism in obese subjects. *Br. J. Nutr.* 1984, 52, 97–105.) However, the same issues described above in tolerance and product development apply to the use of soluble fiber to induce the feeling of fullness and satiety. The commercial market responded to these organoleptic and product stability issues by manufacturing guar gum capsules. However, safety issues surfaced when the capsules were found to stick and swell in the throat upon swallowing. The increased incidence of choking resulted in the guar gum capsules being removed from the market.

Thus, a need has developed in the art for a fiber system that induces the feeling of fullness and satiety, while being well tolerated, organoleptically acceptable and easily incorporated into nutritional matrixes.

The polymer controlled induced viscosity fiber system and acid controlled induced viscosity fiber system filed concurrently herewith by Wolf et. al., each uniquely address the need in the art for a fiber system which slows gastric emptying thereby increasing the feeling of fullness and blunting the absorption curve of carbohydrates after a meal, while being well tolerated, organoleptically acceptable and easily incorporated into nutritional matrixes. However, the clinical effect of each is limited by dilution and acid requirements. For example, natural secretion of stomach juice dilutes the guar gum concentration in the polymer controlled induced viscosity fiber system, which causes the viscosity of the digesta to decrease rather quickly. In order to maintain a high level of digesta viscosity for an extended period of time, higher levels of guar gum are required. As discussed above, the art is full of tolerance and product development issues with guar gum. While better tolerated the previous system, the acid controlled induced viscosity fiber system requires a minimum threshold of stomach secretions to produce a high level of digesta viscosity, thereby delaying the increase in viscosity and building viscosity over time.

SUMMARY OF THE INVENTION

The inventors have been able to develop a fiber system that improves upon the prior art. The dual induced viscosity system addresses the in vivo dilution effect and the soluble fiber tolerance issues, while maintaining a high digesta viscosity for a longer period of time and optimizing the ready-to-feed viscosity of a liquid nutritional product containing guar gum.

The first embodiment of the present invention refers to a nutritional product comprising the dual induced viscosity fiber system. The first component of the induced viscosity fiber system is soluble fiber, said soluble fiber is comprised of neutral soluble fiber and anionic soluble fiber. The second component of the induced viscosity fiber system is lightly hydrolyzed starch. The third component of the induced viscosity fiber system is water-insoluble, acid-soluble multivalent cations.

The present invention also refers to a method of delivering soluble fiber to diabetics and to persons needing to lose weight. The present invention also refers to a method of blunting the postprandial glycemic response of a human by feeding a liquid nutritional product containing the induced viscosity fiber system. Additionally, the invention refers to a method of promoting the feeling of fullness and satiety by feeding a nutritional product containing the induced viscosity fiber system.

DETAILED DESCRIPTION OF THE INVENTION

Figure 1:
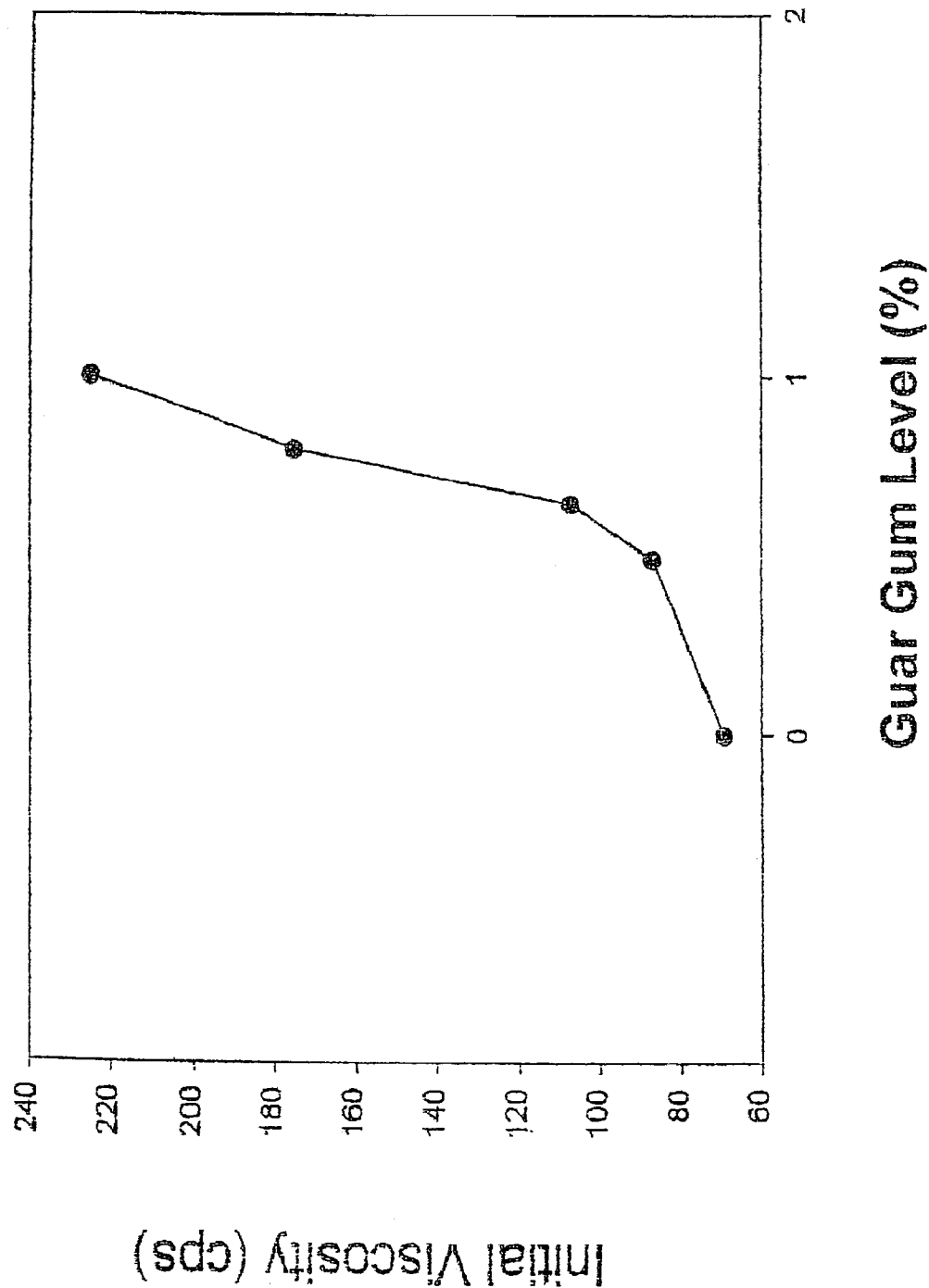
FIG. 1: Effect of guar gum level on the initial viscosity of the meal replacement prototypes.

As used in this application:
a. "glycemic index" (GI) is calculated by dividing the blood glucose incremental area under the curve (AUC) of the test food by the blood glucose AUC of the reference food and multiplying by 100, where the available carbohydrate content of test and reference foods are the same. The reference food is typically glucose or white bread, which has the standard GI of 100.
b. "anionic soluble fiber" refers to water-soluble fibers that carry negative charges after being dissolved in water.
c. "water-insoluble, acid-soluble multivalent cations" refers to salts that are not soluble in water at neutral pH and that will react with acid releasing the cation. Multivalent cations listed in The Merck Index, Tenth Edition as insoluble or practically insoluble in water and soluble in acid are typical examples of suitable salts.

d. "neutral water soluble fiber" refers to fiber that can be dissolved in water and carries no charge at neutral pH.
e. "satiation" refers to the feeling of fullness during a meal. Various gastrointestinal mechanisms trigger the termination of eating in individuals. Although gastric distention is a normal sign of "fullness" and plays a role in controlling food intake, its effects are temporary and distinct from feelings of satiety associated with a meal.
f. "satiety" refers to the feeling of fullness after a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.
g. the term "dextrose equivalence" (DE) refers to a quantitative measure of the degree of starch polymer hydrolysis. It is a measure of reducing power compared to a dextrose (glucose) standard of 100. The higher the DE, the greater the extent of starch hydrolysis. As the starch is further hydrolyzed (higher DE), the average molecular weight decreases and the carbohydrate profile changes accordingly. Maltodextrins have a DE less than 20. Corn syrup solids have a DE of 20 or higher and are rapidly digested and absorbed.
h. the term "degree of polymerization" (DP) refers to the number of glucose units joined in the molecule. The higher the DP average, the lesser the extent of starch hydrolysis. As the starch is further hydrolyzed, the average molecular weight decreases, the average DP decreases and the carbohydrate profile changes accordingly. Maltodextrins have a greater DP than corn syrup solids.
i. the term "starch" refers to the variety of cereal and root starches that contain amylose or amylopectin starch molecules and mixtures thereof.
j. the term "lightly hydrolyzed starch" refers to a product obtained by acid, enzyme or combined hydrolysis of starch consisting of lower molecular weight polysaccharides, oligosaccharides and/or monosaccharides. Hydrolyzed starches typically include acid modified starches, acid thinned starches, thin boiling starches, dextrins and maltodextrins. The lightly hydrolyzed starches suitable for the instant invention typically have a DP of at least about 10.
k. the term "acid requirement" refers to the amount of acid required to ionize the multivalent cation that then cross-links the anionic soluble fiber molecules thereby developing a viscous digesta.
l. "soluble" and "insoluble" dietary fiber is determined using American Association of Cereal Chemists (AACC) Method 32-07. A "soluble" dietary fiber source refers to a fiber source in which at least 60% of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.
m. "fermentable" and "non-fermentable" dietary fiber is determined by the procedure described in "Fermentability of Various Fiber Sources by Human Fecal Bacteria In Vitro", at AMERICAN JOURNAL CLINICAL NUTRITION, 1991; 53:1418–1424. This procedure is also described in U.S. Pat. No. 5,085,883 to Garleb et al. "Non-fermentable" dietary fiber refers to dietary fibers that have a relatively low fermentability of less than 40% by weight, preferably less than 30% by weight, and the term "fermentable" dietary fiber refers to dietary fibers that have a relatively high fermentability of greater than 60% by weight, preferably greater than 70% by weight.
n. the term "total calories" refers to the total caloric content of a definitive weight of the finished nutritional product.
o. the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.
p. the term "in vivo viscosity" refers to the viscosity measured by the addition of 20 μL of bacterial alpha-amylase (Sigma) to 250 gm of sample followed by shearing using a Glass-Col mixer for 30 minutes. The viscosity following shearing is measured using a Brookfield Viscometer (Model DV–II+) with a 62 spindle at room temperature. The enzyme treated samples above are then titrated with acid to determine maximum viscosity. Aliquots (5 ml) of 0.1N HCL were added to the sample while the sample is sheared using a Glass-Col mixer for 30 seconds per milliliter of HCL. The viscosity following shearing is measured using a Brookfield (model DVII+) viscometer with a 62 spindle at room temperature.
q. the term viscosity is the ratio of shear stress to shear rate, expressed as dynes-second/cm$^2$, or poise. A centipoise (cps) is one hundredth of a poise. A poise is a unit of coefficient of viscosity, defined as the tangential force per unit area required to maintain one unit difference in velocity between two parallel planes separated by one centimeter of fluid. Any viscosity determination should be carried out using a Brookfield Viscometer (Model DV–II+) with a 62 spindle at room temperature. The viscosity is measured by operating the viscometer at a spindle speed that is the highest speed possible to obtain a reading that is on scale.
r. any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1–10 should be construed as supporting a range of 2–8, 3–7, 5, 6, 1–9, 3.6–4.6, 3.5–9.9, 1.1–9.9, etc.
s. the terms "induced viscosity fiber system", "dual induced viscosity fiber system", "dual induced viscosity system" and "induced viscosity system" are used interchangeably and refer to the instant invention.

For maximum clinical impact, typically, the induced viscosity fiber system will be incorporated into meal replacement beverages such as Glucerna®, Ensure®, Choice DM®, Slim Fast®, Pediasure®, Glytrol®, Resource® Diabetic, etc. Methods for producing such food products are well known to those skilled in the art. The following discussion is intended to illustrate such diabetic and weight loss meal replacement products and their preparation.

The nutritional formulas of this invention are designed to be used as a meal replacement or as a supplement. Because the product can be used as a meal replacement it will contain a protein source, a lipid source, a carbohydrate source, and vitamins, and minerals. Such amounts are well known by those skilled in the art and can be readily calculated when preparing such products. While these meal replacement products may serve as the sole source of nutrition, they typically don't. Individuals consume these products to replace one or two meals a day, or to provide a healthy snack. The nutritional products of this invention should be construed to include any of these embodiments.

The amount of these nutritional ingredients can vary widely depending upon the targeted patient population (i.e. diabetics vs. non-diabetics, organoleptic considerations, cultural preferences, age, use, etc.). Although not intended to limit the invention in any manner, but to merely serve as a general guideline, the nutritional formulas of this invention will typically provide the following caloric distribution. The protein system will typically provide from about 10% to about 35% of total calories, more preferably from about 15% to about 25% of total calories. The lipid system will provide less than about 37% of total calories, more preferably about 10% to about 30% of total calories. The carbohydrate system will typically provide from about 25% to about 75% of total calories, more preferably from about 35% to about 70% of total calories.

The novelty of these meal replacement products is the successful incorporation of the induced viscosity fiber system that generates viscous digesta over a prolonged period of time upon exposure to alpha amylase and acid.

The first component of the meal replacement products of the instant invention is carbohydrate. The soluble fiber of the induced viscosity fiber system is considered part of the carbohydrate system. Numerous types of dietary fibers are known and available to one practicing the art. Fibers differ significantly in their chemical composition and physical structure and therefore their physiological functions. The dietary fiber sources utilized in this invention can be characterized by the term solubility. Fiber can be divided into soluble and insoluble types and fiber sources differ in the amount of soluble and insoluble fiber they contain.

Representative of soluble dietary fiber sources are gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, 62 -glucans, carrageenan and psyllium. Numerous commercial sources of soluble dietary fibers are readily available and known to one practicing the art. For example, gum arabic, hydrolyzed carboxymethylcellulose, guar gum, xanthan gum, alginates, pectin and the low and high methoxy pectins are available from TIC Gums, Inc. of Belcamp, Md. The oat and barley glucans are available from Mountain Lake Specialty Ingredients, Inc. of Omaha, Nebr. Psyllium is available from the Meer Corporation of North Bergen, N.J. while the carrageenan and konjac flour are available from FMC Corporation of Philadelphia, Pa.

Preferably, one of the soluble-fibers of the instant invention is also anionic. Representative of anionic soluble dietary fiber sources are alginate, pectin, low methoxy pectin, carrageenan, xanthan and gellan gum.

Practitioners typically refer to the total amount (or percentage) of fiber in a serving. The amount of soluble anionic fiber required for the dual induced viscosity fiber system is from about 0.2 wt/wt % to 2.0 wt/wt % of the meal replacement product, preferably from about 0.4 wt/wt % to 1.3 wt/wt % of the meal replacement product, more preferably from about 0.6 wt/wt % to about 1.1 wt/wt % of the meal replacement product. A single meal replacement serving is typically from about 250 gm to about 350 gm.

Any single anionic fiber listed above, or any combination thereof may be utilized in the induced viscosity fiber system of the instant invention. The preferred anionic soluble fiber source is alginate because it is less viscous and less fermentable than other soluble fibers. Alginate is the salt of alginic acid and is isolated from brown seaweed, family Phaeophyceae. It is composed of mannuronic (pKa~3.38) and guluronic acid (pKa~3.65). Alginate, in the absence of free polyvalent cations, is a relatively nonviscous soluble fiber. Alginate solutions gel upon addition of free calcium ions, which fill the cavities formed between parallel guluronic acid chains. These cavities contain two carboxylate and two hydroxyl groups, one from each chain.

Preferably, the induced viscosity system comprises a second soluble fiber that is neutral. Representative of neutral soluble dietary fiber sources are guar gum, pectin, locust bean gum, methylcellulose, β-glucans, glucomannan, and konjac flour.

The amount of neutral soluble fiber required for the dual induced viscosity fiber system is from about 0.2 wt/wt % to 2.0 wt/wt % of the meal replacement product, preferably from about 0.4 wt/wt % to 1.3 wt/wt % of the meal replacement product, more preferably from about 0.6 wt/wt % to about 1.1 wt/wt % of the meal replacement product.

The preferred neutral soluble fiber source is guar gum. Experiment 1 describes the effect different levels of guar gum had on the ready-to-feed viscosity of meal replacement products manufactured as described in Example 1. All of the levels generated viscosity below 300 cps. Guar gum is a viscous, water-soluble dietary fiber composed of a β-1,4 mannose backbone with galactose side chains linked α-1,6. This galactomannan is obtained from the endosperm of the seeds of the leguminous vegetable, Indian cluster bean, *Cyamposis tetragonolobus*. It is widely used in the food industry as a stabilizer and as a thickening and film-forming agent.

A third more soluble carbohydrate is required for the induced viscosity fiber system of the instant invention to function. Typically, the preferred more soluble carbohydrate is lightly hydrolyzed starch. The concentration of the starch required to prevent the neutral soluble fiber from dissolving is inversely proportional to the molecular weight of the starch. Useful hydrolyzed starches of the instant invention typically comprise a DP of at least about 10, preferably of at least about 20, more preferably from about 40 to about 100.

Representative of suitable starch sources are cornstarch, potato starch, beet starch, rice starch, tapioca starch, and wheat starch and combinations thereof. Numerous commercial sources of starch and hydrolyzed starch are readily available and known to one practicing the art. For example, maltodextrin, glucose polymers, hydrolyzed cornstarch are available from Cerestar in Hammond, Ind. Wheat, rice and cornstarches are available from Weetabix Company in Clinton, Mass. Potato starch is available from Staley Mfg. Company in Decatur, Ill.

Alternatively, hydrolyzed starch may be obtained by acid, enzyme or combined hydrolysis of starch. One practicing the art would be aware of suitable hydrolysis methods. Typically, acid modified starches are made by mild acid hydrolysis of starch. For example, granular starch is suspended in very dilute acid and held at a temperature below its gelatinization temperature to yield an acid modified or thin boiling starch. Maltodextrins are typically prepared by partial hydrolysis of cornstarch with acids and enzymes.

Dextrins are typically prepared by a process called pyrolysis, which involves a dry reaction with heat and acid.

Any single lightly hydrolyzed starch listed above, or any combination thereof may be utilized for the dual induced viscosity fiber system of the instant invention. The amount of lightly hydrolyzed starch required for the dual induced viscosity fiber system is from about 3.0 wt/wt % to 15.0 wt/wt % of the meal replacement product, preferably from about 3.0 wt/wt % to 10.0 wt/wt % of the meal replacement product.

The remaining portion of the carbohydrate system may be provided by any carbohydrate system suitable for humans, taking into account any relevant dietary restrictions (i.e. if intended for a diabetic). As indicated above, the carbohydrate typically contributes from about 25% to about 75% of total calories. Examples of suitable carbohydrates that may be utilized include glucose polymers, sucrose, honey, sugar alcohols, corn syrup solids, glucose, fructose, lactose, and high fructose corn syrup.

In addition to the carbohydrates described above, the nutritionals may also contain indigestible oligosaccharides such as fructooligosaccharides (FOS). Indigestible oligosaccharides are rapidly and extensively fermented to short chain fatty acids by anaerobic microorganisms that inhabit the large bowel. These oligosaccharides are preferential energy sources for most *Bifidobacterium* species, but are not utilized by potentially pathogenic organisms such as *Clostridium perfingens, C. difficile,* or *E coli*. The term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

An example of a typical carbohydrate system comprises 6.5 wt/wt % of the carbohydrate system as alginate, 5.6 wt/wt % of the carbohydrate system as guar gum, 23 wt/wt % of the carbohydrate system as fructose, 20 wt/wt % of the carbohydrate system as maltitol, 4 w/w % of the carbohydrate system as FOS and 41wt/wt % of the carbohydrate system as maltodextrin DE1

The meal replacement products also typically contain a protein source. The proteins that may be utilized in the nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein, mineral enriched proteins and mixtures thereof. Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

As discussed above, the protein system will typically provide from about 10% to about 35% of total calories. When selecting an appropriate protein source, one skilled in the art is aware that native protein can trap the soluble fiber in globules preventing it from cross-linking with the ionized salts. Additionally, protein can carry carboxy groups that will compete with the anionic soluble fiber for the ionized calcium resulting in an increase in the acid requirement. Further the solubility of the protein source can impact the solubility of the neutral soluble fiber.

An example of a typical protein system comprises about 55 wt/wt % heat denatured whey protein, about 20 wt/wt % whey protein isolate and about 25 wt/wt % sodium caseinate.

The third component of the nutritional products of this invention is the fat. The fat source for the present invention may be any fat source or blend of fat sources suitable for human consumption. As noted above, the fat source of this invention will typically provide less than or equal to 37% of the total calories. The fat source for the present invention may be any fat source or blend of fat sources which provides the desired levels of saturated (less than 10% kcal), polyunsaturated (up to 10% kcal) and monounsaturated fatty acids (10% to 15% kcal). One skilled in the art can readily calculate how much of a fat source should be added to the nutritional product in order to deliver the desired levels of saturated, polyunsaturated and monounsaturated fatty acids. Examples of food grade fats are well known in the art and typically include soy oil, olive oil, marine oil, sunflower oil, high oleic sunflower oil, safflower oil, flax seed oil, high oleic safflower oil, fractionated coconut oil, cottonseed oil, corn oil, canola oil, palm oil, palm kernel oil and mixtures thereof.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Organ. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

The nutritional compositions of the invention desirably contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micro nutrients such as ascorbic acid due to higher turnover in people with diabetes.

The fourth component of the induced viscosity fiber system is water-insoluble multivalent cations that are ionized under acidic conditions.

Representative of water-insoluble multivalent cation sources that are acid-soluble are magnesium, calcium, iron, chromium, manganese, molybdenum, copper, zinc, calcium carbonate, calcium fluoride, calcium molybdate, calcium oxalate, calcium phosphate dibasic, calcium phosphate tribasic, calcium pyrophosphate, calcium saccharate, magnesium fluoride, magnesium hydroxide, magnesium oxide, magnesium peroxide, magnesium phosphate tribasic, magnesium pyrophosphate, magnesium selenite, manganese carbonate, manganese oxide, manganese sulfide and combinations thereof. Numerous commercial sources water-insoluble, acid-soluble multivalent cation sources are readily available and known to one practicing the art. For example, tricalcium phosphate is available from Fortitech in Schenectady, N.Y. Calcium carbonate is available from Specialty Minerals Inc. in Bethleham, Pa. Magnesium phosphate is. available from Jost Chemicals in St. Louis, Mo. Calcium phosphate monobasic is available from Monsanto Company in St. Louis, Mo.

Any single multivalent cation listed above, or any combination thereof may be utilized in the induced viscosity fiber system of the instant invention. The preferred multivalent cation source is calcium carbonate. Since, free calcium is the preferred "trigger" to cross link alginate, levels of free calcium are typically less than 40 ppm.

An example of the vitamin and mineral system for a nutritional formulation used as a meal replacement typically comprises at least 20% of the RDI for the vitamins A, $B_1$, $B_2$, $B_6$, $B_{12}$, C, D, E, K, beta-carotene, biotin, folic acid, pantothenic acid, niacin, and choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in a single serving or from about 50 Kcal to about 1000 Kcal. This level of minerals typically supplies sufficient multivalent cations to support the induced viscosity fiber system.

Artificial sweeteners may also be added to the nutritional formula to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include strawberry, peach, butter pecan, chocolate, banana, raspberry, orange, blueberry and vanilla.

Upon digestion, the induced viscosity fiber system is exposed to alpha amylase which begins to digest the lightly hydrolyzed starch, enabling the neutral soluble fiber to become solubilized. Meanwhile, as the stomach secretions increase and the pH drops, the acid ionizes the multivalent cation that cross-links the anionic soluble fiber increasing the digesta viscosity, The induced viscosity fiber system of the instant invention generates a viscous digesta resulting in the slow release of nutrients into the small intestine. The slow release of nutrients into the small intestine results in prolonged absorption of nutrients, thereby blunting the glycemic response to the meal. The viscosity generated in vivo by the induced viscosity fiber system is greater than about 300 cps, preferably at least about 1000 cps, more preferably at least 3000 cps.

Preferably, the induced viscosity fiber system is formulated to produce maximum viscosity with minimum acid requirement. The induced viscosity fiber system is formulated to require less than about 120 ml of acid per 250 gm of product, preferable less than about 60 ml of acid per 250 gm product.

The induced viscosity fiber system has been designed to generate optimal viscosity in vivo while minimizing the ready-to-feed viscosity. The ready-to-feed viscosity of the induced viscosity fiber system is less than about 300 cps, preferably less than about 200 cps, more preferably from about 50 cps to about 150 cps.

The nutritional products of this invention can be manufactured using techniques well known to those skilled in the art. While manufacturing variations are certainly well known to those skilled in the nutritional formulation arts, a few of the manufacturing techniques are described in detail in the Examples. Generally speaking a fiber in oil blend is prepared containing all oils, soluble fiber, any emulsifier, stabilizer and the fat soluble vitamins. Three more slurries (protein and two carbohydrate) are prepared separately by mixing a part of the carbohydrate and minerals together, the remaining carbohydrate with the fiber and the protein in water. The protein in water and carbohydrate/mineral slurries are then mixed together with the oil blend. The resulting mixture is homogenized, heat processed, standardized with water soluble vitamins, and flavor. The final blend is homogenized and aseptically filled in to appropriate containers. Alternatively, the homogenized formula may be kept undiluted and dried to form powder. The product is then packaged. Typically the package will provide directions for use by the end consumer (i.e. to be consumed by a diabetic, to assist with weight loss, etc.).

A second embodiment of the instant invention is a method of blunting the postprandial glycemic response in a human by feeding the induced viscosity fiber system described above. The method may be used for nutritional management of persons with diabetes, for people with insulin resistance as well as a preventative therapy for high-risk populations (e.g., obese and first degree relatives of people with type 2 diabetes mellitus).

A third embodiment of the instant invention is a method of promoting the feeling of fullness in a human by feeding the induced viscosity fiber system described above. The inventors discovered, in Experiment 3, that nutritional products containing the induced viscosity fiber system would delay gastric emptying thereby increasing the feeling of fullness.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention. The following non-limiting Examples will further illustrate the present invention.

EXPERIMENT 1

Initial experimentation evaluated the effect different levels of guar gum had on the initial viscosity of a prototype containing 0.75% alginate, calcium carbonate and DE 1 maltodextrin. The product was manufactured as described in Example 1 below using 0, 0.5, 0.65, 0.8 and 1% guar gum. FIG. 1 plots the effect of guar gum level on the initial viscosity of the prototypes.

EXPERIMENT 2

Figure 2:
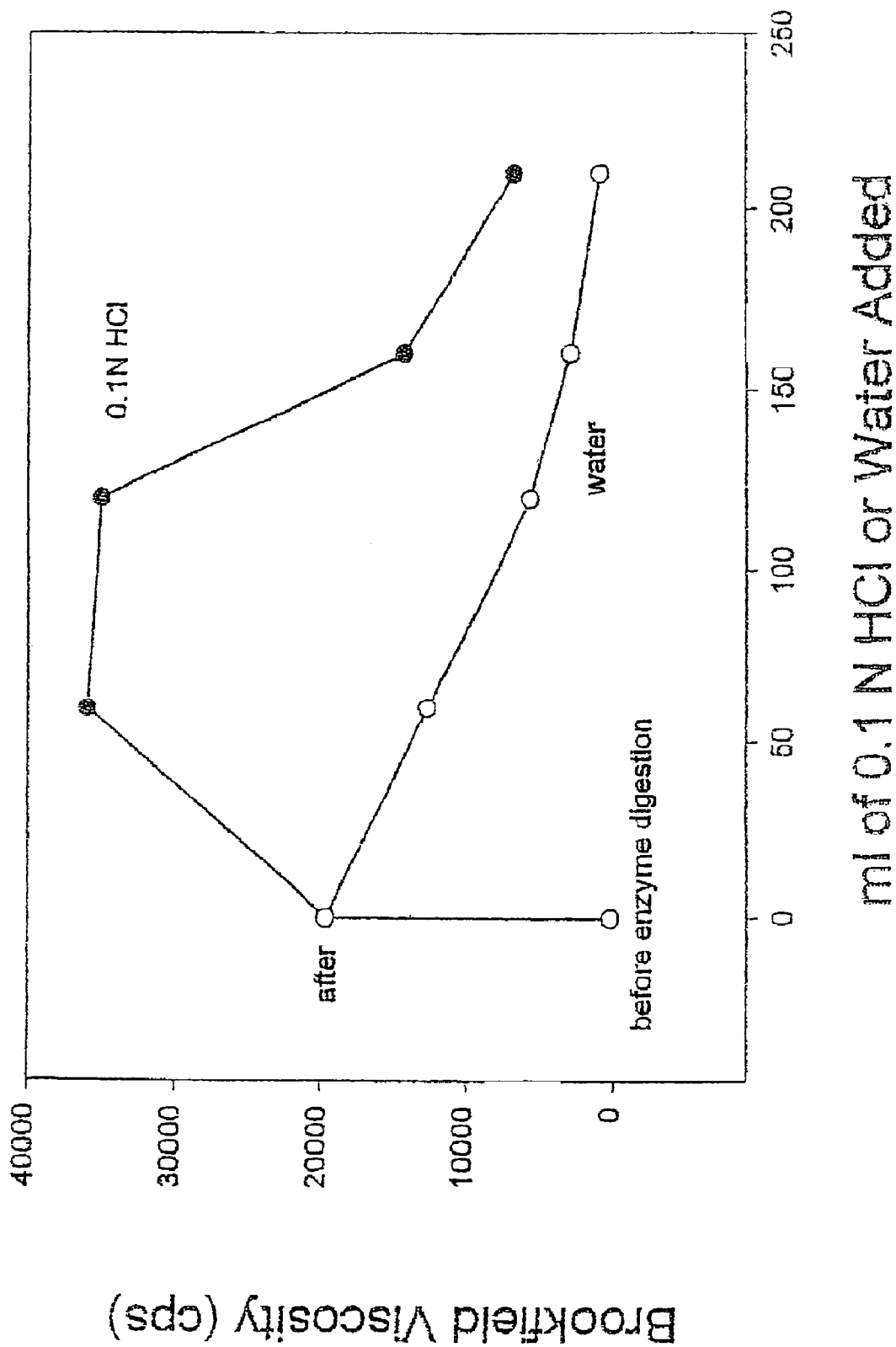
FIG. 2: Viscosity of meal replacement prototype after enzyme and acid treatment.

The 0.75% alginate/1% guar gum prototypes above were digested with alpha amylase. The induced viscosity increased from 200 cps to over 19,000 cps (FIG. 2). Diluting the enzyme treated mix with water caused a drastic reduction in viscosity. Adding 0.1N HCL to the enzyme treated product caused the viscosity of the simulated digesta to increase to over 30,000 cps.

EXAMPLE 1

The manufacture of 454 kg of a nutritional product that contains the dual induced viscosity fiber system of the instant invention is described below. The required amounts of ingredients (Table 1) for the fiber in fat slurry were combined and held.

TABLE 1

| Fiber in Fat Slurry | |
| --- | --- |
| High oleic safflower oil | 8 kg |
| Canola oil | 961 gm |
| Soy lecithin | 480 gm |
| Vitamin DEK premix* | 30.87 gm |
| Beta carotene 30% | 1.6 kg |
| Vitamin A palmitate | 1.5 kg |
| Sodium alginate | 2.7 kg |
| Potassium alginate | 680 gm |

*per gm Vitamin DEK premix: 8130 IU vitamin $D_3$, 838 IU vitamin E, 1.42 mg vitamin $K_1$ The required amount of ingredients (Table 2) for the protein in water slurry were combined. The pH was adjusted to 6.7 to 6.9 using 1 N KOH and the blend was held.

TABLE 2

| Protein in Water Slurry | |
| --- | --- |
| Water | 193 kg |
| Na caseinate | 4 kg |
| Whey protein isolate | 4 kg |
| Alacen | 9.5 kg |

The required amount of ingredients (Table 3) for the carbohydrate/mineral slurry were combined. The pH was adjusted to 6.8 to 7.0 using 1N KOH and the blend was held.

TABLE 3

| Carbohydrate/Mineral Slurry | |
| --- | --- |
| Water | 28 kg |
| Maltodextrin DE1 | 11 kg |
| Fructose | 2.7 kg |
| Tricalcium phosphate | 1.8 kg |
| Magnesium phosphate dibasic | 1.4 kg |
| Potassium chloride | 1.1 kg |
| UTM/TM premix* | 136 gm |
| Ca carbonate | 68 gm |
| Potassium iodide | 0.11 gm |

*per gm of UTM/TM premix: 83 mg zinc, 65 mg iron, 18 mg manganese, 7.8 mg copper, 0.262 mg selenium, 0.365 mg chromium, 0.585 molybdenum.

After each slurry was prepared, the carbohydrate/mineral slurry was added to the protein in water slurry. The blend pH was adjusted to 6.6–6.8. The fiber in fat slurry was then added to the blend. The blend was processed at UHT temperatures (295° F. for 5 seconds) and homogenized at 4000 psi.

The required amount of ingredients (Table 4) for the vitamin solution were combined and the pH was adjusted to 6.9 to 7.1 using 45% KOH. The pH adjusted solution was held.

TABLE 4

| Vitamin Solution | |
| --- | --- |
| Water | 7.6 kg |
| Ascorbic acid | 227 gm |
| Choline chloride | 45 gm |
| L-Carnitine | 50 gm |
| WSV premix* | 36 gm |
| Taurine | 45 gm |
| Vanilla flavor | 2 kg |
| Sucralose | 74 gm |

*per gm of WSV premix: 375 mg niacinamide, 242 mg calcium pantothenate, 8.4 mg folic acid, 62 mg thiamine chloride, 48 mg riboflavin, 59 mg pyridoxine hydrochloride, 165 mcg cyanocobalamin, and 7305 mcg biotin The vitamin solution was added to the processed blend at standardization The required amount of ingredients (Table 5) for the 3% guar gum solution were combined and the pH was adjusted to 6.5 to 7.5 using 1 N KOH. The blend was held.

TABLE 5

| Guar Gum Solution | |
| --- | --- |
| Water | 113 kg |
| Maltodextrin DE1 | 25 kg |
| Guar gum | 47 kg |

The guar gum solution was added to the standardized blend. Guar gum was added to the maltodextrin solution under high agitation to prevent build up of excessively high viscosity and guar gum lumps. Failure to disperse guar gum properly caused flow problems in the aseptic filling unit. The final blend was UHT heated to 295° F. for 5 seconds and homogenized at 1000 psi and aseptically filled into sterile 32 oz bottles.

EXPERIMENT 3

The primary objective was to compare satiety after consumption of induced-viscosity products with control products in healthy male subjects by measuring caloric intake following a preload. The supporting objectives were to evaluate the effect of induced-viscosity study products on subjective fullness after a preload, and to evaluate subjective gastrointestinal tolerance compared with the control products, i.e. nausea, abdominal cramping, distention, and flatulence.

Adult male subjects who met all eligibility criteria were enrolled into the study. The experiment followed a randomized, double-masked, crossover design. Subjects were asked to avoid vigorous exercise for the 48 hours prior to each test. Subjects were also asked to refrain from drinking alcohol on the day before each study day and throughout each study day. On the night before the test, subjects were asked to keep their activity level and evening meal as normal as possible, and to refrain from eating or drinking after 10 p.m. Only water was allowed during fasting.

Before the start of the study, subjects selected their beverages for breakfast (coffee, tea, orange juice, or milk, or a combination thereof). At the beginning of each test day, subjects consumed breakfast ad libitum (this ensured that subjects were at the same level of satiety at the initiation of each preload). Breakfast included their selected beverages as well as bagels, cream cheese, grape jelly, and strawberry jam. Randomized subjects arrived at the test site around 8:00 a.m. on the study day. They were asked sensory and satiety related questions before and after breakfast and questions regarding meal intake and activity of the night before. Subjects were instructed not to consume any food or beverages, except water, in the interval between breakfast and the preload. After three hours, subjects again were asked sensory and satiety related questions. The subjects consumed their randomized treatment (preload) before a prepared and weighed lunch meal. Each preload contained approximately 220 kcal (served chilled, 4° C., in a cup with a lid and straw). Subjects had 10 minutes to consume their preload and were given preset timers to pace their consumption. Lunch was served approximately 30 minutes after subjects initiated preload consumption. After consuming as much lunch as desired, subjects completed questionnaires about their feelings of satiety for approximately 5 hours. Subjects were answered questions on subjective gastrointestinal tolerance for the 24-hour period post-preload. During the preload and lunch meal, subjects were seated in individual cubicles.

Before each preload was served, subjects rated 30-mL samples of the preload on 100-mm visual analogue scales (VAS). The following sensory attributes were rated: pleasantness of taste, perceived "fat" content, texture, sweetness, creaminess, and prospective consumption. After they completed the ratings, subjects were served the preload. Upon completion of the preload, subjects again received a 30-mL sample and were asked to rate the above sensory attributes.

Lunch was an individual, buffet-style, self-selected meal that allowed participants to choose ad libitum from a variety of meal-appropriate foods (same foods were available for each test day). The foods varied in fat, carbohydrate, and protein contents to allow subjects to vary their energy intake and proportions of macronutrients. Each of the subjects were randomized to receive all four treatments on four separate days: SlimFast® control, maltodextrin control, induced-viscosity product with guar gum (polymer controlled induced viscosity fiber system), and induced-viscosity product with guar gum and alginate (dual induced viscosity fiber system). The study days were scheduled approximately every seven days. The study staff verified study product intake for each subject during each of the five treatment days. Subjects consumed the study product, and compliance was recorded on a worksheet. Subjects could be rescheduled due to noncompliance with the study procedures. Subjects underwent a mock trial day in which SlimFast® was served as the preload (prior to the evaluation of the four treatments). This enabled the study staff and subjects to become familiar with the study procedures. As planned, these data were not included for data analysis.

Male subjects were chosen for this study to eliminate variability, and because healthy lean men are often used in satiety studies as they are good predictors of the general population for eating patterns and have a tendency to be less restrictive in their eating patterns.

Subjects were eligible for the study if they were 21 years of age or older, male, had a body mass index (BMI) between 20 and 28 kg/m$^2$, had no known allergies to any of the ingredients in the study products or to any of the main food items being served during lunch (e.g., dairy, wheat, turkey), regularly ate three meals per day, agreed not to participate in other nutritional or drug studies until he had completed the present study, and had not participated in a study for at least one month prior to study screening, and had voluntarily signed and personally dated an informed consent form prior to any participation in the study.

Subjects were ineligible for the study if they were using prescription or non-prescription medications or supplements that could affect appetite and food intake, according to the clinical judgment of the PI and/or study physician, smoked, were trying to lose or gain weight or was an athlete-in-training, had active metabolic or gastrointestinal diseases that may interfere with nutrient absorption, distribution, metabolism, or excretion, had swallowing difficulties, had a score $\geq 30$ on the eating attitudes test (Garner, D. M.; Garfinkel, P. E. The Eating Attitudes Test: an index of the symptoms of anorexia nervosa. *Psychol. Med.* 1979, 9, 273–280. ), or a score >8 for the cognitive restraint subscale in the eating inventory questionnaire (Stunkard, A. J.; Messick, S. The three-factor eating questionnaire to measure dietary restraint, disinhibition, and hunger. *J. Psychosom. Res.* 1985, 29, 71–83. ), or $\geq 40$ on the Zung self-rating questionnaire (Zung, W. W. K. A self-rating depression scale. *Arch. Gen. Psychiatry* 1970, 12, 63–70), and disliked vanilla shakes or $\geq 2$ of the main food items to be served in any of the test meals.

The study visits were grouped into three categories: Screening, Treatment, and Study Exit. The screening visit was conducted prior to the start of the study. The objectives of the screening visit were to verify eligibility for the trial, secure informed consent from the subject, and collect entrance demographics (age, race, height, weight, medical history, eating inventory, eating attitudes test, Zung questionnaire, etc.) and current medications. The subjects were then randomized once they met eligibility requirements.

At each treatment visit the subjects were questioned about compliance to study procedures and prohibited medications. Noncompliance could result in rescheduling or removal from the study; subjects consumed breakfast (~8:00 a.m.) and completed a sensory/satiety questionnaire before and after breakfast; subjects were given randomized test product as a preload (at ~11 a.m. or noon) and provided a sensory evaluation/satiety questionnaire before and after the preload. Once a subject completed the preload, they were not rescheduled for a make-up date for that visit; subjects consumed a prepared and weighed lunch meal 30 minutes after start of preload consumption (~11:30 a.m. or 12:30 p.m.); subjects completed a sensory/satiety questionnaire for approximately 5 hours postprandial; subjects recorded frequency and intensity of GI tolerance factors for the 24-hour period following treatment consumption.

Subjects rated feelings of satiety before and after breakfast, preload, and lunch, and hourly for approximately 5 hours after lunch. Prior to completing a treatment preload, subjects completed a mock study day so that they were familiar with the study procedures and requirements.

The exit visit was conducted at the conclusion of the study no later than one week after the last day of the final treatment period, or upon withdrawal from the study.

Four treatments were evaluated in this experiment: 1) SlimFast® French Vanilla (SlimFast® Foods Company, West Palm Beach, Fla.) nutritional control, 2) maltodextrin control (MC), 3) induced-viscosity product containing 0.65% guar gum and 0.75% alginate, and 4) induced-viscosity product containing 1.0% guar gum and 0.75% alginate. A more detailed description of the products is found in Table 6 below.

TABLE 6

Macronutrient composition of SlimFast ® and experimental products

| | SlimFast ® | Maltodextrin-based control (MC) | 0.65% guar gum, 0.75% alginate (IV/low) | 1.0% guar gum, 0.75% alginate (IV/high) |
|---|---|---|---|---|
| | gm/200 kcal (% of total calories) | | | |
| Fat | 3 (12) | 7 (29) | 7 (29) | 7 (29) |
| Carbo-hydrate | 40 (70) | 33 (51) | 33 (51) | 33 (51) |
| Dietary fiber | 5 | 5 | 5 | 5 |
| Protein | 10 (18) | 11 (20) | 11 (20) | 11 (20) |

All products were formulated to have similar appearance and taste (vanilla) compared with SlimFast®. The initial viscosity of the maltodextrin control was 39.2 cps, while the induced-viscosity variables had the following initial viscosity: IV/high was 357 cps and IV/low was 294 cps.

The secondary variables were ratings of satiety [fullness, hunger, thirst, nausea, and prospective consumption (how much food they think they could eat)] and sensory characteristics (pleasantness of taste, texture, sweetness, and creaminess, perceived "fat" content, and prospective consumption) of the nutritional beverage (preload). Subjective ratings of fullness were recorded on a 100-mm line (i.e., visual analogue scale) preceded by the question "How full do you feel right now?" and anchored on the left by "not at all full" and on the right by "extremely full". Likewise, hunger, thirst, and nausea were anchored with the phrases "not at all" and "extremely". Prospective consumption was preceded by the question "How much food do you think you could eat right now" and anchored on the left by "nothing at all" and on the right by "a large amount". Ratings were completed before and after breakfast, preload, and lunch, and then hourly for 5 hours after lunch. Pleasantness of taste etc. was evaluated by the question "How pleasant is the taste (or other sensory attribute) of the nutritional beverage right now?" and anchored on the left by "not at all pleasant" and on the right by "extremely pleasant". Perceived "caloric" content was evaluated by the question "How much fat do you think the nutritional drink has?" anchored on the left by "no fat at all" and on the right by "extremely high in fat". In addition, the proportions of macronutrients (fat, protein, and carbohydrate) consumed during the lunch meal were calculated.

Using a questionnaire, subjects recorded subjective tolerance factors for intensity and frequency of gastrointestinal symptoms (nausea, abdominal cramping, distention and flatulence) for the 24 hours after the test. Intensity and frequency are set to a 100-mm line scale (0 representing "Absent" and 100 "Severe" and 0 representing "Less than usual" and 100 "More than usual," respectively).

The average age, weight; height, and BMI of the subjects were 37.6±1.5 years, 76.7±1.6 kg (169±3.4 lb), 1.8±0.0 m (69.5±0.5 in), and 24.6±0.4 kg/m$^2$ respectively. In addition, the mean subject scores for the eating attitudes test, cognitive restraint test, and the Zung self-rating questionnaire were 11.7±0.4, 5.0±0.3, and 30.0 ±0.9 respectively.

RESULTS

The primary variable for this study was caloric intake at the lunch meal. In the Intent-to-treat (ITT) population, there was a significant difference detected (p=0.046) between the products for calories consumed as the liquid product. However, the Tukey-Kramer adjusted comparisons among the least squares means did not identify any pair wise differences at p<0.05. Subjects consuming the IV/low consumed approximately 100 calories less at lunch compared with when subjects consumed the SlimFast® product as the preload. However, there were no significant differences (p<0.05) detected either for calories consumed at the lunch meal or for the total caloric intake (combining the lunch meal and liquid product). In addition, no statistical differences were detected in either analysis (ITT or PE) for weight of food consumed or the percentage of calories from fat, protein, or carbohydrate at the lunch meal.

The study products in this experiment were not found to be unsafe. Of the four gastrointestinal tolerance variables (nausea, cramping, distention, and flatulence) analyzed for frequency and intensity, the only statistically significant finding was nausea at a greater frequency in study product IV/high (high induced-viscosity product 1.0% guar gum, 0.75% alginate) compared with SlimFast®.

The secondary variables were ratings of satiety [fullness, hunger, thirst, nausea, and prospective consumption (how much food they think they could eat)] and sensory characteristics (pleasantness of taste, texture, sweetness, and creaminess, perceived "fat" content, and prospective consumption) of the nutritional beverage (preload). For the fullness rating, the two induced-viscosity products (IV/high, IV/low) were greater (p<0.05) than SlimFast® after the preload. At two hours after lunch, study products IV/high and IV/low were greater (p<0.05) than SlimFast® (See Table 7).

TABLE 7

How full do you feel right now?

Dietary Treatment (Intent-to-treat analysis)

| | SlimFast ® | Maltodex-trin based control (MC) | 0.65% guar gum, 0.75% alginate (IV/low) | 1.0% guar gum, 0.75% alginate (IV/high) |
|---|---|---|---|---|
| Before Bkfast | 19 ± 3 | 21 ± 4 | 27 ± 5 | 23 ± 4 |
| After Bkfast | 64 ± 3 | 66 ± 3 | 66 ± 2 | 61 ± 4 |
| Before Preload | 25 ± 3 | 27 ± 4 | 26 ± 4 | 22 ± 3 |
| After Preload | 47 ± 4[b] | 52 ± 4[a,b] | 56 ± 3[a] | 58 ± 4[a] |
| After Lunch | | | | |
| 0 hr | 85 ± 2 | 86 ± 2 | 86 ± 2 | 84 ± 2 |
| 1 hr | 73 ± 4 | 77 ± 3 | 79 ± 2 | 77 ± 3 |
| 2 hr | 61 ± 5[b] | 67 ± 3[a,b] | 72 ± 3[a] | 70 ± 4[a] |
| 3 hr | 53 ± 4 | 57 ± 4 | 57 ± 4 | 57 ± 4 |
| 4 hr | 43 ± 4 | 44 ± 5 | 48 ± 4 | 50 ± 4 |
| 5 hr | 32 ± 5 | 30 ± 5 | 33 ± 4 | 40 ± 5 |
| 5-hr AUC | 17679 ± 963 | 18176 ± 914 | 19082 ± 848 | 18969 ± 917 |

0 = "not full at all", 100 = "extremely full".
Means with unlike superscripts are significantly different, p < 0.05

For the prospective consumption rating, at four and five hours after lunch subjects noted that they could eat more after consuming the two control products compared with IV/high product in both analyses. In the PE analysis only, the maltodextrin based control was greater (p<0.05) than IV/high after the preload (See Table 8).

TABLE 8

How much food do you think you could eat right now?

Dietary Treatments
(intent to treat analysis)

| | SlimFast ® | Maltodextrin-based control (MC) | 0.65% guar gum, 0.75% alginate (IV/high) | 1.0% guar gum, 0.75% alginate (IV/low) |
|---|---|---|---|---|
| Before Bkfast | 60 ± 3 | 60 ± 4 | 59 ± 4 | 60 ± 4 |
| After Bkfast | 25 ± 3 | 25 ± 2 | 30 ± 3 | 32 ± 3 |
| Before Preload | 63 ± 4 | 66 ± 3 | 67 ± 3 | 67 ± 3 |
| After Preload | 45 ± 3 | 47 ± 3 | 42 ± 3 | 39 ± 3 |
| After Lunch | | | | |
| 0 hr | 9 ± | 10 ± 2 | 9 ± 2 | 10 ± 2 |
| 1 hr | 16 ± 2 | 16 ± 2 | 13 ± 2 | 13 ± 2 |
| 2 hr | 22 ± 3 | 21 ± 3 | 19 ± 3 | 18 ± 3 |
| 3 hr | 34 ± 4 | 31 ± 4 | 28 ± 3 | 27 ± 3 |
| 4 hr | 44 ± 4 | 46 ± 5[b] | 41 ± 4[a,b] | 34 ± 4[a] |
| 5 hr | 58 ± 5 | 60 ± 5[b] | 54 ± 5[a,b] | 49 ± 4[a] |
| 5-hr AUC | 8788 ± 823[b] | 8936 ± 851 | 7969 ± 771[a,] | 7277 ± 803[a] |

0 = "nothing at all". 100 = "a large amount"
Means with unlike superscripts are significantly different, p < 0.05

For the hunger rating, maltodextrin based control was greater (p<0.05) than IV/high after the preload in both analyses, and both control products were greater (p<0.05) than IV/high at four and five hours after lunch for both analyses (See Table 9).

TABLE 9

How hungry do you feel right now?

Dietary Treatments
(Intent-to-treat analysis)

| | SlimFast ® | Maltodextrin-based control (MC) | 0.65% guar gum, 0.75% alginate (IV/high) | 1.0% guar gum, 0.75% alginate (IV/low) |
|---|---|---|---|---|
| Before Bkfast | 65 ± 4 | 64 ± 4 | 57 ± 4 | 64 ± 4 |
| After Bkfast | 24 ± 3 | 22 ± 3 | 23 ± 3 | 21 ± 3 |
| Before Preload | 63 ± 4 | 60 ± 4 | 67 ± 3 | 66 ± 3 |
| After Preload | 44 ± 3[a,] | 47 ± 3[b] | 42 ± 3[a,b] | 36 ± 3[a] |
| After Lunch | | | | |
| 0 hr | 7 ± | 7 ± 2 | 8 ± 3 | 7 ± 1 |
| 1 hr | 12 ± 2 | 12 ± 2 | 9 ± 2 | 11 ± 2 |
| 2 hr | 17 ± 3 | 20 ± 3 | 18 ± 3 | 15 ± 3 |
| 3 hr | 32 ± 3 | 30 ± 3 | 29 ± 3 | 23 ± 3 |
| 4 hr | 44 ± 4 | 46 ± 5[b] | 38 ± 4[a,b] | 32 ± 4[a] |
| 5 hr | 59 ± 5 | 61 ± 5[b] | 53 ± 5[a,b] | 47 ± 4[a] |
| 5-hr AUC | 8106 ± 757[b] | 8477 ± 813[b] | 7549 ± 788[a,] | 6475 ± 799[a] |

0 = "not at all, 100 = "extremely"
Means with unlike superscripts are significantly different, p < 0.05

In the ITT population only, subjects had a higher rating for nausea after consuming the IV/high product compared with SlimFast®, and maltodextrin based control products (p<0.05). For the thirst variable after the preload, study product IV/low (and IV/high in the PE analysis) caused greater thirst (p<0.05) than SlimFast® in both analyses.

Overall, the two control products (SlimFast® and MC) were perceived to have a more pleasant taste, texture, creaminess, and sweetness than the study products IV/high and IV/low. The two control products were also perceived by subjects to be lower in fat than the other three products; and subjects reported that they could consume more of the two control products than IV/high and IV/low products.

CONSLUSION

Based on the results of this study, the two dual fiber induced-viscosity products IV/high and IV/low appear to increase satiety and decrease caloric intake at a meal after consumption of a preload (study product). Subjects felt full longer after consuming these two products compared with the control products. In addition, consumption of IV/high resulted in subjects feeling less hunger and resulted in lowered prospective consumption at four and five hours post-lunch compared with the control products.

We claim:

1. A method for blunting the postprandial glycemic response of an individual comprising administering to said individual a meal replacement product comprising:
   (a) from about 3.0 to about 15.0% by weight of a lightly hydrolyzed starch having a DP of at least about 10, and
   (b) from about 0.2 to about 2.0% by weight of a neutral soluble fiber source that is solubilized following alpha amylase digestion of the lightly hydrolyzed starch In the stomach, and
   (c) from about 0.2 to about 2.0% by weight of an anionic water-soluble fiber source, and
   (d) a water-insoluble, acid-soluble, multivalent cation source that is ionized in the stomach following administration,
   wherein the meal replacement product contains less than about 40 ppm of free calcium, and after administration generates an in vivo-viscosity of greater than about 300 cps.

2. The method according to claim 1 wherein said anionic soluble fiber source is selected from the group consisting of alginate, pectin, low methoxy pectin, carrageenan, xanthan and gellan gum and mixtures thereof.

3. The method according to claim 1 wherein said water-insoluble, acid-soluble, multivalent cation source is selected from the group consisting of calcium carbonate, calcium fluoride, calcium molybdate, calcium oxalate, calcium phosphate dibasic, calcium phosphate tribasic, calcium pyrophosphate, calcium saccharate, magnesium fluoride, magnesium hydroxide, magnesium oxide, magnesium peroxide, magnesium phosphate tribasic, magnesium pyrophosphate, magnesium selenite, manganese carbonate, manganese oxide, manganese sulfide and combinations thereof.

4. The method according to claim 1 wherein said neutral soluble fiber source is selected from the group consisting of guar gum, locust bean gum, methylcellulose, β-glucans, glucomannan, and konjac flour and mixtures thereof.

5. The method according to claim 1 wherein the meal replacement product after administration generates an in-vivo viscosity greater than about 3000 cps.

6. The method according to claim 1 wherein the meal replacement product is a ready-to-feed liquid having a viscosity of less than 300 cps.

7. The method according to claim 6 in which said meal replacement comprises:
   a. protein providing from about 10 to about 35% of total calories,
   b. fat providing less than about 37% of total calories, and
   c. carbohydrate providing from about 25 to about 75 % of total calories.

8. The method according to claim 1 wherein the water-insoluble, acid-soluble, multivalent cation source comprises calcium carbonate.

* * * * *